(12) United States Patent
Rosenthal

(10) Patent No.: US 7,591,556 B2
(45) Date of Patent: Sep. 22, 2009

(54) SCLERAL CONTACT LENS WITH GROOVES AND METHOD OF MAKING LENS

(75) Inventor: Perry Rosenthal, Needham, MA (US)

(73) Assignee: Boston Foundation for Sight, Needham, MA (US)

( * ) Notice: Subject to any disclaimer, the term of this patent is extended or adjusted under 35 U.S.C. 154(b) by 17 days.

(21) Appl. No.: 11/473,290

(22) Filed: Jun. 22, 2006

(65) Prior Publication Data

US 2006/0290883 A1    Dec. 28, 2006

Related U.S. Application Data

(60) Provisional application No. 60/753,893, filed on Dec. 22, 2005, provisional application No. 60/693,857, filed on Jun. 24, 2005.

(51) Int. Cl.
*G02C 7/04* (2006.01)

(52) U.S. Cl. .................. 351/160 R; 351/159

(58) Field of Classification Search ............ 351/160 R, 351/161–162, 160 H
See application file for complete search history.

(56) References Cited

U.S. PATENT DOCUMENTS

| | | | | |
|---|---|---|---|---|
| 2,117,770 A | * | 5/1938 | Row ..................... | 351/160 R |
| 2,989,894 A | * | 6/1961 | Gordon ................. | 351/160 R |
| 4,621,912 A | * | 11/1986 | Meyer .................. | 351/160 R |
| 5,104,213 A | * | 4/1992 | Wolfson ............... | 351/160 R |
| 5,166,710 A | * | 11/1992 | Hofer et al. ........... | 351/160 R |
| 5,500,695 A | * | 3/1996 | Newman ............... | 351/161 |
| 5,815,236 A | | 9/1998 | Vayntraub | |
| 5,815,237 A | | 9/1998 | Vayntraub | |
| 5,975,694 A | | 11/1999 | Vayntraub | |
| 6,082,856 A | | 7/2000 | Dunn et al. | |
| 6,095,651 A | | 8/2000 | Williams et al. | |

(Continued)

OTHER PUBLICATIONS

Rosenthal et al. "Fluid-Ventilated, Gas-Permeable Scleral Contact Lens Is an Effective Option for Managing Severe Ocular Surface Disease and Many Corneal Disorders that Would Otherwise Require Penetrating Keratoplasty," Reprinted from Eye & Contact Lens, vol. 31, No. 3, May 2005, pp. 130-134.

(Continued)

*Primary Examiner*—Ricky L Mack
*Assistant Examiner*—James R Greece
(74) *Attorney, Agent, or Firm*—Wilmer Cutler Pickering Hale & Dorr LLP.

(57) ABSTRACT

The present invention provides a scleral lens which includes channels on its posterior bearing surface that improve the flow of tears between the bearing surface of the device and the underlying scleral eyes tissue into the space between the optic of the lens and cornea. The channels are disposed on the inside surface of the lens and extend generally radially from the inside of the haptic and the outside rim of the lens. Various configurations are possible for the channels, as described in more detail below. Additionally, the channels can have a serpentine or arcuate configuration to allow for the appropriate amount of fluid flow between the space under the lens and the scleral surface of the eye. In another embodiment, microchannels can be formed in the lens to increase the oxygen permeability of the lens. The microchannels can have many configurations that reduce the volume of the lens material.

13 Claims, 4 Drawing Sheets

U.S. PATENT DOCUMENTS

| | | | |
|---|---|---|---|
| 6,145,988 | A | 11/2000 | Manfredini et al. |
| 6,176,579 | B1 | 1/2001 | Mandell |
| 6,199,986 | B1 | 3/2001 | Williams et al. |
| 6,206,520 | B1 | 3/2001 | Jubin et al. |
| 6,241,355 | B1 | 6/2001 | Barsky |
| 6,270,221 | B1 | 8/2001 | Liang et al. |
| 6,271,914 | B1 | 8/2001 | Frey et al. |
| 6,271,915 | B1 | 8/2001 | Frey et al. |
| 6,299,311 | B1 | 10/2001 | Williams et al. |
| 6,305,802 | B1 | 10/2001 | Roffman et al. |
| 6,340,229 | B1 | 1/2002 | Lieberman et al. |
| 6,364,482 | B1 | 4/2002 | Roffman et al. |
| 6,379,005 | B1 | 4/2002 | Williams et al. |
| 6,406,145 | B1 | 6/2002 | Jubin |
| 6,419,359 | B2 | 7/2002 | Edwards |
| 6,454,409 | B1 | 9/2002 | Lorenz et al. |
| 6,491,392 | B2 | 12/2002 | Roffman et al. |
| 6,497,483 | B2 | 12/2002 | Frey et al. |
| 6,499,843 | B1 | 12/2002 | Cox et al. |
| 6,554,427 | B1 | 4/2003 | Davis et al. |
| 6,558,586 | B1 | 5/2003 | Padiou et al. |
| 6,569,154 | B2 | 5/2003 | Campin et al. |
| 6,578,963 | B2 | 6/2003 | Pettit |
| 6,586,499 | B2 | 7/2003 | Bonafini, Jr. et al. |
| 6,595,639 | B1 | 7/2003 | Ho et al. |
| 6,595,640 | B1 | 7/2003 | Jubin |
| 6,779,888 | B2 | 8/2004 | Marmo |
| 2002/0021409 | A1* | 2/2002 | Marmo ............... 351/160 R |
| 2005/0119739 | A1 | 6/2005 | Glazier |

OTHER PUBLICATIONS

Romero-Rangel, et al., "Gas-permeable Scleral Contact Lense Therapy in Ocular Surface Disease," American Journal of Ophthalmology, vol. 130, Jul. 2000, pp. 25-32.

Rosenthal, et al. "Treatment of Persistent Corneal Epithelial Defect With Extended Wear of a Fluid-ventilated Gas-permeable Scleral Contact Lens," American Journal of Ophthalmology, Jul. 2000, pp. 33-41.

Schein, et al., "A Gas-Permeable Scleral Contact Lens for Visual Rehabilitation," American Journal of Ophthalmology, Mar. 1990, pp. 318-322.

New Contact Lens Lets Blind See, Boston, Sep. 4, 2003, 1 page.

Bruce R. Lakefield, "Seeing is Believing," US Airways Attache, Sep. 2004, 1 page.

Kelly Egan, "Bringing Back the Gift of Sight Puts a Whole Life Back in Focus," The Otawa Citizen, 2 pages.

Melba Newsome, "Out of the Darkness," Good Housekeeping, Feb. 2006, pp. 119-120.

Blood & Marrow Transplant Newsletter, "A Site for Sore Eyes," http://www.bmtinfonet, 3 pages.

Cheryl Guttman, "Scleral Lens an Important Tool in Many 'last resort' Scenarios," Ophthalmology Times, Sep. 1, 2005, 1 page.

Abigail Sullivan Moore, "A New Lens Restores Vision and Brings Relief," The New York Times, Jul. 1, 2003, 2 pages.

Patent Cooperation Treaty, International Search Report, dated Jan. 31, 2008, 2 pages.

* cited by examiner

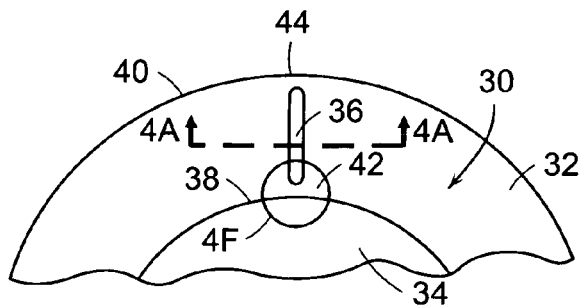
FIG. 4
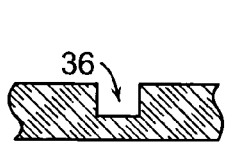
FIG. 4A
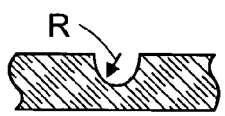
FIG. 4B
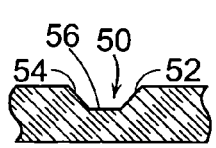
FIG. 4C
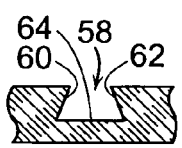
FIG. 4D
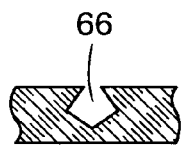
FIG. 4E
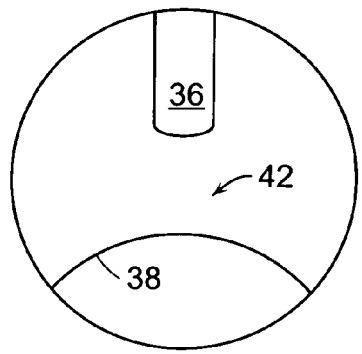
FIG. 4F
FIG. 4G
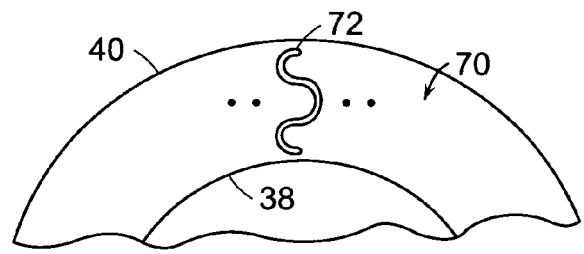
FIG. 5
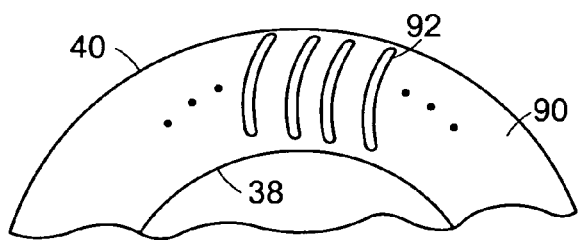
FIG. 6
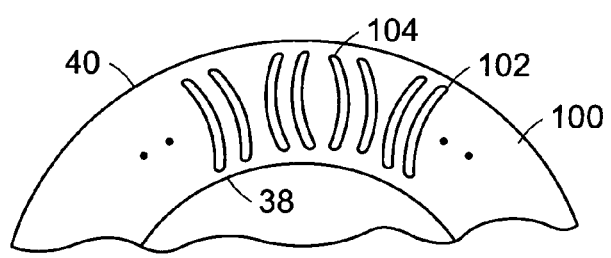
FIG. 7

SCLERAL CONTACT LENS WITH GROOVES AND METHOD OF MAKING LENS

CROSS REFERENCE

This application claims the benefit of priority to U.S. Provisional Application Ser. No. 60/693,857 filed Jun. 24, 2005, the disclosure of which is incorporated by reference herein in its entirety. This application also claims the benefit of priority to U.S. Provisional Application Ser. No. 60/753,893 filed Dec. 22, 2005, the disclosure of which is incorporated by reference herein in its entirety.

TECHNICAL FIELD

This disclosure relates generally to a scleral lens with grooves for aspirating tears to prevent suction when the lens is disposed on the eye. Also, this disclosure relates to a method of making the lens using laser technology.

BACKGROUND

The cornea is the transparent dome-shaped front part of our eyes and their most important focusing lens. Like the lens of a camera, its surface must be perfectly smooth in order to provide clear vision. When disease or injury causes the corneal surface to become irregular, the eye can no longer focus clearly, even with the strongest glasses. Hard contact lenses have the unique ability to improve the vision of these eyes by creating a smooth layer of tears that optically masks the irregular surface of the cornea. However, there are many eyes with damaged corneas that cannot be fitted with a hard contact lens that rests on their corneas. Moreover, the corneas of patients who suffer from severe ocular surface disease become so exquisitely fragile that they are often unable to withstand the pressure of blinking or the briefest exposure to air and even less so the friction of a hard contact lens.

A scleral lens, such as the Boston Scleral Lens offered by the Boston Foundation for Sight, provides a device that addresses this condition. As shown in FIGS. 1-3 and 3A, a scleral lens 10, which is about the size of a quarter, rests on the relatively insensitive white sclera 12 of the eye 14 and creates a space 16 over the cornea 18 that is filled with artificial tears. The eye contact location for the scleral lens is different than conventional contact lenses which rest on the cornea. As illustrated by the contact length L in FIG. 2, contact with the eye is limited to the sclera and the lens does not contact the cornea 18. By creating a fluid-filled space over the irregular surface of the damaged cornea, this lens device can be helpful in improving vision in eyes with extremely distorted corneas. Moreover, this fluid compartment becomes a liquid bandage that protects the raw and sensitive cornea from exposure to air and the rubbing effects of blinking. The therapeutic environment created between the lens and the cornea nurtures healing and can virtually eliminate pain and photosensitivity. It is this unique "corneal liquid bandage" that is responsible for the extraordinary healing experienced by patients who have used the scleral lens. However, by sealing a pool of liquid over the cornea, the scleral lens simulates a fluid pump by which micro quantities of fluid are squeezed out of the fluid compartment during lens compression as occurs during blinking. When the lens is decompressed after each blink, tears outside the lens are drawn into the fluid compartment. If the aspiration of tears is blocked during lens decompression, negative pressure develops in the fluid compartment that increases over time resulting in progressive lens suction that can be severely damaging to the eye. The traditional solution to scleral lens suction is to drill a hole in the lens through which air is aspirated (air ventilated). However, the presence of air bubbles in the fluid compartment causes desiccation of the corneal surface that is especially dangerous for diseased corneas. The purpose of this invention is to create a mechanism for preventing lens suction by facilitating the aspiration of outside tears while excluding the transit of air bubbles.

A groove 22 is provided in that part of the posterior contact lens surface that rests on the scleral surface of the eye (haptic). More than one groove is typically used. The groove(s) allows tears outside the lens to be aspirated into the central fluid compartment to prevent the development of suction.

One of the reasons for the effectiveness of the Boston Scleral Lens is its highly oxygen-porous plastic, developed under the leadership of Boston Foundation for Sight founder Dr. Perry Rosenthal, that allows the cornea to breathe through the lens. The cornea, unlike any other surface tissue of the human body breathes by extracting oxygen directly from the surrounding air rather than from the blood circulation and the oxygen porous plastic allows oxygen to reach the surface of the eye.

A scleral lens can be beneficial to treat a number of conditions. Among the most common conditions treated is severe dry eye. Some causes of dry eyes are an underlying medical condition, such as Sjogren's syndrome, graft versus host disease (following bone marrow transplants), radiation treatment in the eye area, Stevens-Johnson syndrome, and autoimmune disorders. In some cases the cause is unknown (idiopathic). The condition can be due to a diminished supply of tears, excessively rapid evaporation or both. Dry eyes is one of the most common ocular complaints. Symptoms vary from mildly annoying, intermittent dryness and burning and paradoxical tearing (worse in dry environments) to constant disabling pain, increased light sensitivity and blurred vision. Mild to moderate cases of dry eyes can usually be controlled by the frequent use of artificial tears, punctal plugs that slow the drainage of tears from the eyes and a new, prescription eye drop (Restasis) that may reduce the inflammation associated with dry eyes. This group constitutes the vast majority of dry eyes. However, it is the patient with severe, disabling dry eyes unresponsive to the above treatments who can benefit the most from the Boston Scleral Lens device (BSL) and for whom scleral lens is being prescribed.

It is important to treat severe dry eyes, which is one of the conditions known as severe ocular surface disease. Such patients suffer constant disabling eye pain and photosensitivity and may develop erosions on the surface of their corneas that impair vision and can lead to scarring and permanent impairment of vision. In the most severe cases, corneal ulcers develop that are slow to heal (if they heal at all) and can result in perforation. Rarely, it may be necessary to suture the lids together in order to save the eye (tarsorrhaphy). These severely dry eyes are more prone to infection and heal so poorly that surgery, including corneal transplant, is rarely successful and even dangerous. Conventional treatments described above are of little value. The so-called soft bandage lens is often ineffective because it requires an adequate supply of tears to maintain its hydration.

Keratoconus is another eye condition can be addressed by the use of a scleral lens. Keratoconus is characterized by a progressive thinning and steepening of the central cornea. As the cornea steepens and thins, a patient experiences a decrease in vision which can be mild or severe depending on the severity of the disease. Keratoconus has no known cure.

Onset of keratoconus occurs during the teenage years—mean age of onset is age 16 years—but onset has been reported to occur at ages as young as 6 years. Keratoconus shows no gender predilection and is bilateral in over 90% of cases. In general, the disease develops asymmetrically: diagnosis of the disease in the second eye lags about five years after diagnosis in the first. The disease process is active for about five to 10 years, then it may be stable for many years. During the active stage, change may be rapid.

Typically, early vision loss can be corrected by spectacles; later, irregular astigmatism requires optical correction with rigid contact lenses. Hard contact lenses provide a uniform refracting surface and therefore improve vision. However, traditional rigid contact lenses rest on the surface of the cornea and slide over this surface with each blink. As a result, patients with diseased or damaged corneas who are most likely to benefit from their unique vision-restoring properties are often unable to tolerate them and would face the potential serious complications and uncertain visual outcome of corneal transplant surgery.

An estimated hundreds of thousands of patients suffering from corneal disorders in the U.S. alone can benefit from the Foundation's lenses. The vast majority of patients are young-some are children. The Boston Scleral Lens is their only hope for regaining function vision. For the remaining patients, our lenses replace the need for corneal transplant surgery. The cornerstone of the Boston Scleral Lens is the liquid bandage it sustains over the corneal surface. This device is the first fluid-ventilated gas-permeable scleral lens designed to maintain an oxygenated aqueous corneal environment free of air bubbles. Lens suction is avoided by incorporating a series of radial channels in the posterior haptic surface that facilitates the aspiration of tears (while excluding air) as the means of aborting the development of negative hydrostatic pressure.

In order to avoid obstructing the channels (a prerequisite to the physiological tolerance of the devices), the shape of each haptic bearing surface is adapted to the contour of the underlying sclera through the design/fitting process. This flexibility and precision has been made possible by a process described in U.S. Pat. No. 5,452,031, the entire contents of which is incorporated by reference. Based on advanced mathematical functions known as "splines", the design program has been integrated with the control system of the state-of-the-art contact lens lathe. This on-site technology has been an essential resource for advancing the development of the Foundation's lenses and enabling us to reach a success rate exceeding 90%. The oxygen tension of the corneal liquid bandage is maintained by a highly oxygen permeable polymer from which the devices are fabricated. Specially manufactured discs of this material are made for the Boston Scleral Lenses by Bausch & Lomb.

The process of making and adapting the shape of scleral lenses to that of the individual eye is exacting and time consuming. Additionally, various channels can be used to enable tears outside the lens to be aspirated into the liquid reservoir between the lens and cornea to abort the development of lens suctions, a highly dangerous situation. At the same time, it is necessary to design the channels to avoid the aspiration of air into the fluid reservoir that would adversely affect the health of the cornea. In order to maintain the patency of the channels, it is necessary to match the shape of the bearing surface of the scleral lens (haptic) with that of the underlying eye surface (sclera) in order to avoid excessive eye compression that would obstruct the channels and render them ineffective. It would be beneficial to enhance the performance of the scleral lens by configuring the groves in manner that makes them less vulnerable to compression or enabling the transit of air bubbles and thereby reduce the precision now required in customizing the shape of their haptic bearing surface.

SUMMARY

Accordingly, the present invention provides a new scleral lens that allows for improved flow of liquid between the bearing surface of the lens (haptic) and the underlying sclera of the eye into the fluid reservoir between the lens and the cornea. The channels in the scleral lens extend radially from the inside border of the scleral contacting surface of the lens (haptic). The channels can have several different configurations that assist in the transit of fluid or tears between the fluid reservoir under the central zone of the lens (optic) and the tears external to the lens. The channels may have a U-shaped cross-section, a V-shaped cross section, a beveled cross-section and others. Further, the cross-section can vary along the radial extension of the channel. Plural channels may be used. Also, the channels may have a serpentine configuration or generally arcuate configuration.

The present invention also provides a novel method of allowing more oxygen to permeate through the lens to the corneal surface. Microchambers within the lens material can assist in increasing the permeability of the lens by decreasing the volume of plastic through which oxygen would have to travel to reach the cornea. The microchambers would be in various configurations in the lens portion of the scleral lens.

BRIEF DESCRIPTION OF THE DRAWINGS

In the Drawings:

FIG. 4 is a detail view of a channel of the present invention;

FIG. 4A is a sectional view taken from lines 4A-4A in FIG. 4;

FIGS. 4B-4E are various configurations of the channel;

FIG. 4F is an expanded view of circle 4F in FIG. 4;

FIG. 4G is an expanded view of an alternative embodiment of a scleral lens taken at the same location as FIG. 4F.

FIGS. 5-7 are various configurations of multiple channels in the scleral lens.

DETAILED DESCRIPTION

The present invention provides a scleral lens which includes channels that improve the flow of tears outside the lens into the fluid reservoir occupying the space between the scleral lens and the cornea. The channels are disposed on the inside surface of the lens and extend generally radially from the inner limits of the scleral contact portion of the lens to the outside rim of the lens. Various configurations are possible for the channels, as described in more detail below. Additionally, the channels can have a serpentine or arcuate configuration to allow for the appropriate amount of fluid flow between the space under the lens and the scleral surface of the eye while preventing the transit of air bubbles. In another embodiment, microchannels can be formed in the lens to increase the oxygen transmissibility of the lens. The microchannels can have many configurations that reduce the volume of the lens material.

Figure 1:
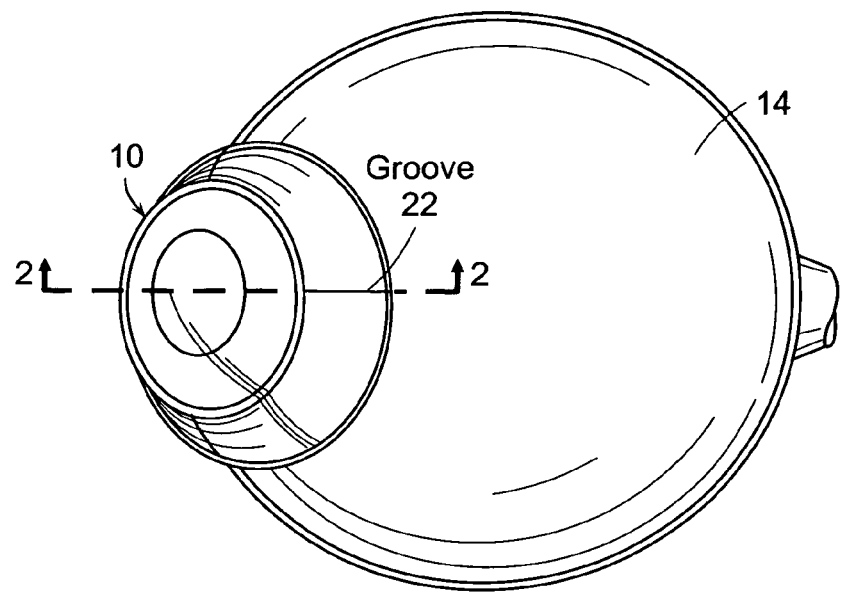
FIG. 1 is a perspective view of an eye with a Boston Foundation for Sight scleral lens.
Figure 2:
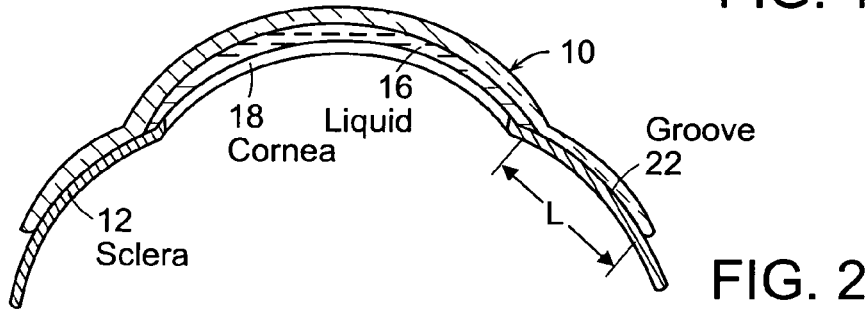
FIG. 2 is a sectional view taken from lines 2-2 in FIG. 1.
Figure 3:
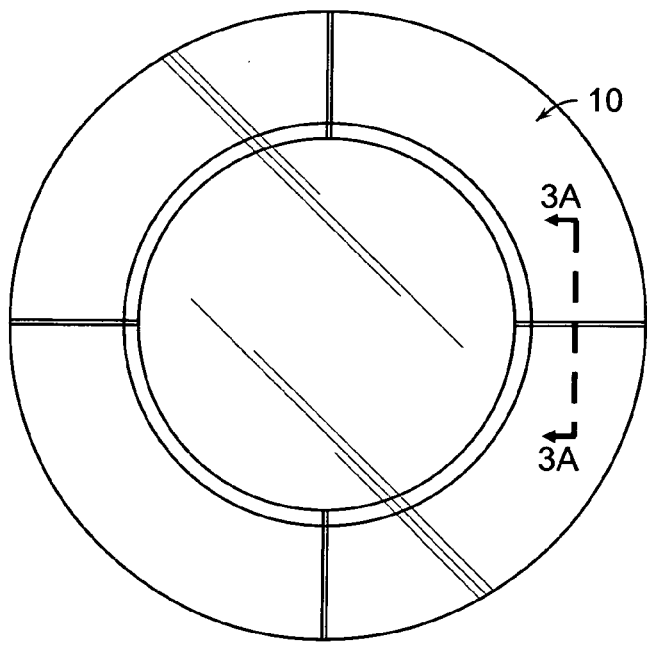
FIG. 3 is a top view of a scleral lens.
Figure 3A:
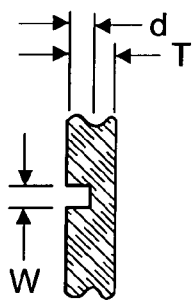
FIG. 3A is a sectional view of the lens taken from lines 3A-3A in FIG. 3.

As illustrated in FIG. 4, a portion of a scleral lens 30 includes both a scleral contact surface 32 and a lens portion 34. The lens portion is disposed above the cornea when the scleral lens is applied to any eye. The scleral surface contacts the lens at the scleral contact surface 32. A channel 36 is disposed in the area of the scleral contact surface 32. The channel may extend between the inside limit of the haptic 38 and the outside rim 40 of the contact lens scleral bearing surface. The channel illustrated in FIG. 3 extends the entire distance between the inside rim and the outside rim of the scleral bearing surfacd. In alternate embodiments the channel may extend the entire distance between the inside rim and the outside rim or it may terminate before the outside rim as illustrated in FIG. 4. When the channel terminated before the inside rim 38 and/or the outside rim 40 an area 42 and 44 may be created which is discussed in more detail below.

The channel 36 may have one or more of several different cross-sections. As illustrated in FIG. 4A, the channel may have a generally square cross-section. Of course, one skilled in the art will be able to modify the choice of dimensions to allow for improved fluid flow into the central fluid compartment after the lens is decompressed following each blink while blocking the transit of air bubbles and tear particulate matter. The number of channels can be selected up to approximately 36. The channels can be evenly distributed along the scleral contact surface or, depending on desired fluid flow characteristics, can be placed unevenly around the scleral contact surface.

As illustrated in FIG. 4B, a channel 48 may have a U shaped cross-section. This may provide advantages such as improved tear flow and a decrease in particulate matter getting caught in the "corners" of the channel. Of course, alternatives to a symmetrical U-share exist within the scope of this invention. For example, depending on the radius R of the curve that creates the U-shape the bottom of the channel 48 could be shallow or have steeper edges. A preferred radius R is about one half the width of the channel.

Other cross-sections can be used. For example, FIG. 4C illustrates a channel 50 with angled side walls 52, 54 and bottom 56. The side walls can create any angle over 90 degrees. FIG. 4D illustrates a channel 58 with angled side walls 60 and 62 which include an angle less than 90 degrees with the bottom 64 of the channel 58. Another alternative construction is illustrated in FIG. 4E where a channel 66 has cross section is in the shape of a diamond. Of course, the various shapes described can be combined to form hybrid cross sections that provide the necessary fluid flow.

As described previously, the channels may terminate before the rims 38 and 40 as illustrated in FIG. 4. FIG. 4F provides a detail view of the space 42 between the channel 36 and the inside rim 38. The distance between the rim and the channel can be significant in developing the proper amount of fluid flow over the scleral surface. In an embodiment where the channels do not extend to the rim(s) the fluid a micro channel 46 may be created to allow for the improved conduction of fluid from the inner space above the cornea and the channel 36. A microchannel can be disposed on the other side of the channel 36. The microchannel may have any of the cross sectional shaped described above. FIG. 4G illustrates a groove 46 that is smaller than the groove 36 which can assist in the hydrodynamics at the surface of the eye. As illustrated the groove is smaller than the groove 36 and extends the distance between the lens portion and the end of the groove. Other configurations are possible such the groove geometries disclosed above.

The cross sections described above may vary in dimension along their axial length. For example, a channel in the radially inward portion of the scleral surface may increase as the channel extends radially outward. In one embodiment, the channel may increase in any dimension by 3 or more times along the length. Additionally, the cross sectional dimensions of a channel may decrease as the channel extends radially outwardly.

As illustrated in FIG. 5-7, the radially extending channels can have different configurations. For example, FIG. 5 illustrates a scleral lens 70 with a channel having a serpentine configuration. The illustrated serpentine configuration has 3 curves, of course more or fewer curves could be used in accordance with the present invention. Multiple serpentine patterns may be formed into the scleral contact area of the lens. The preferred number is up to 36. As illustrated in FIGS. 6 and 7 the scleral lenses 90 and 100 can have arcuate grooves 92 and 102, 104. The arcuate channels may have a small radius (which makes a sharper curve) or a larger radius (which makes a gradually sloping curve). These curves may extend to the rims 38 and 40 of the scleral lens surfaces.

Figure 8:
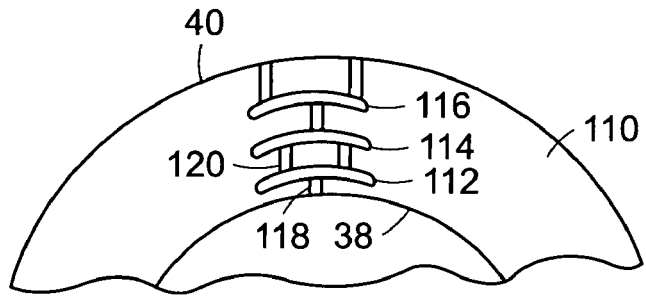
FIG. 8 is an alternate embodiment of the channels.

FIG. 8 illustrates still another embodiment of the present invention where channels are provided that are oriented both circumferentially and radially. Specifically, a scleral lens 110 includes arcuate channels 112, 114, and 116 that are oriented circumferentially. The channels may have any cross section as described above. Further, the arcuate channels can be connected by one or more radial channels 118, 120. As illustrated the number of radial channels may be selected to adjust the amount of fluid that moves between the inner rim 38 and the outer rim 40.

Figure 9:
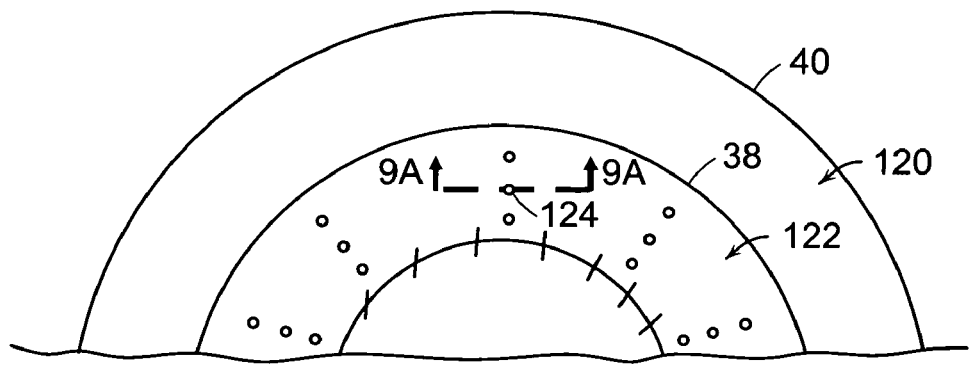
FIG. 9 is an illustration of the microchambers.
Figure 9A:
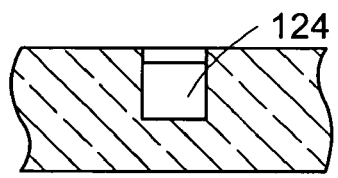
FIG. 9A is a sectional taken from 9A-9A in FIG. 9.
Figure 10:
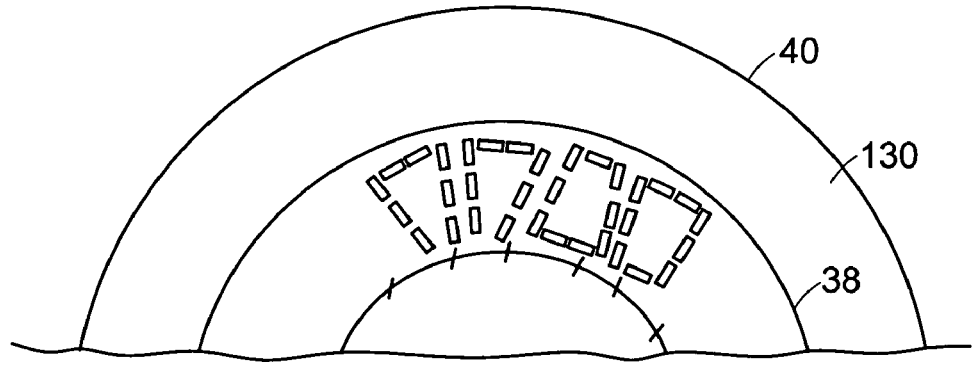
FIG. 10 is an illustration of the configuration of microchambers for the scleral lens.
Figure 11:
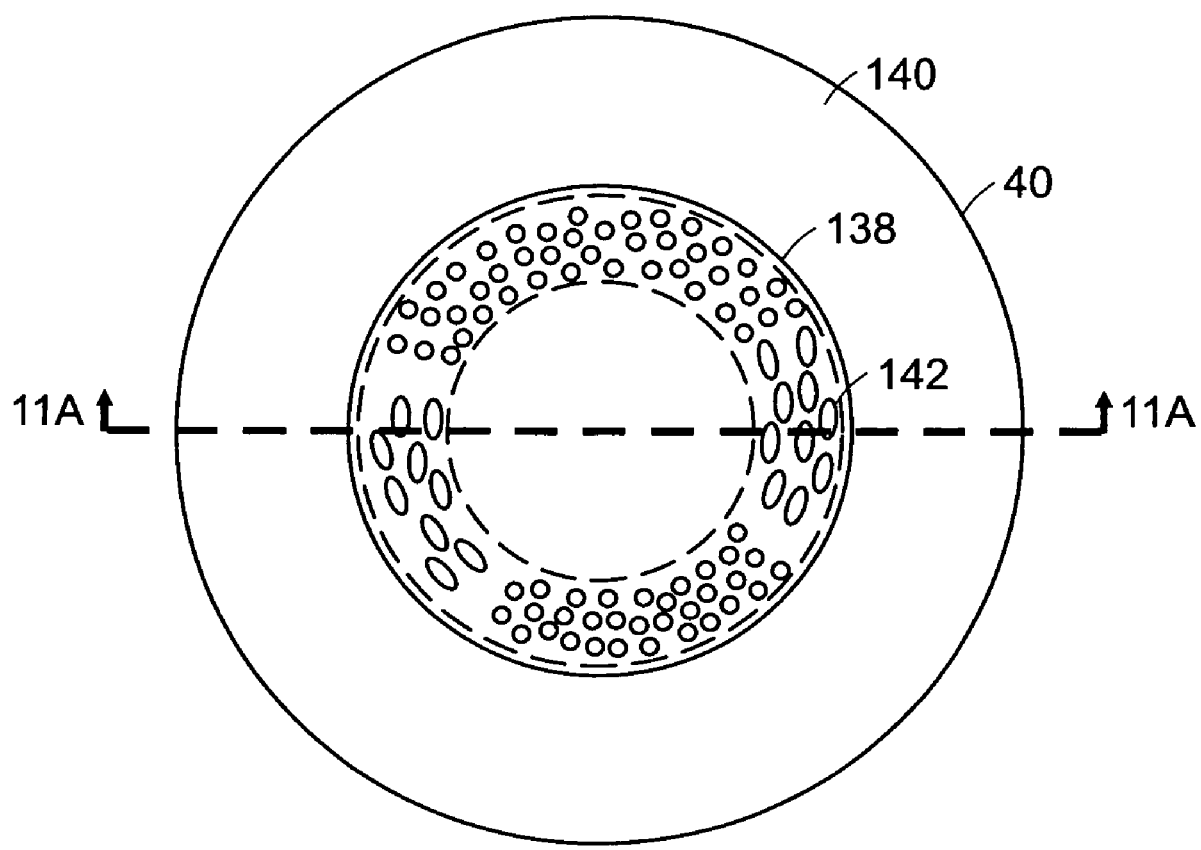
FIG. 11 is a top view of a scleral lens with a microchambers.

FIGS. 9-11 illustrate another embodiment of the present invention where microchambers are formed in the scleral lens so that more oxygen can permeate the lens and provide more safety and comfort to the wearer. Because the cornea, unlike all other tissues of the human body, breathes by extracting oxygen directly from the ambient air, covering the outside surface of the cornea with a sheet of plastic can deprive the cornea of needed oxygen and cause undesirable side effects. Another aspect of the present invention provides microchambers in the optic portion of the scleral lens. In FIG. 9 a scleral lens 120 includes an inner rim 38 and outer rim 40. Microchambers are provided on the optic portion 122 of the scleral lens. The optic portion is disposed above the cornea when the lens is placed on the eye. As illustrated in FIG. 9 and detailed in FIG. 9A, a microchamber 124 is provided that form voids within the lens material. The microchambers increase the gas transmissibility of the lens and enhances the amount of oxygen that can reach the cornea. The microchamber can have the dimensions that allow for increased gas transmissiblity while maintaining structural integrity of the lens itself. As illustrated, three microchambers extend radially along a rim portion of the lens.

As illustrated in FIG. 10, the orientation of the microchamber may be designed to allow for maximum gas transmissibility enhancement while minimizing the loss of structural integrity to the lens. FIG. 10 illustrates a lens 130 with rims 38 and 40 and the microchambers 132 are disposed in rectangular orientation with longer arcuate array of microchambers 132 being disposed at the portion that is disposed by the inner rim 38.

Figure 11A:
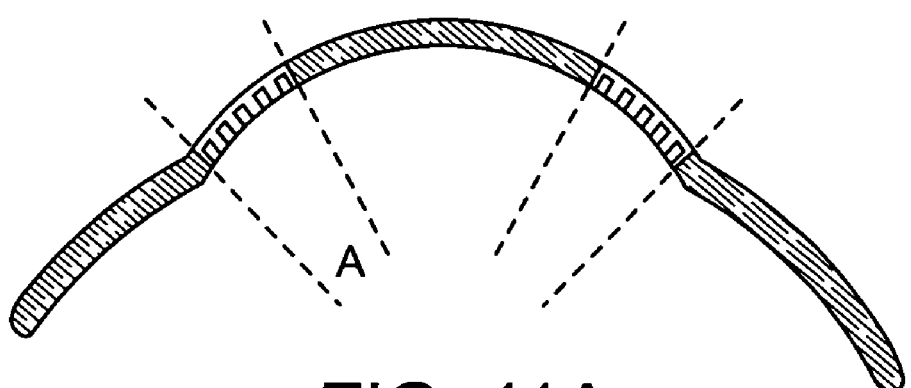
FIG. 11A is a sectional view of a scleral lens taken from lines 11A-11A.

FIGS. 11 and 11A illustrate a scleral lens 140 with an array of microchambers 142 disposed the entire circumference at the outer portion the lens. FIG. 11A illustrates the zone of the array of microchambers that forms a circumferential ring. Such a configuration allows for viewing through the lens to be unobstructed in the event that the microchambers diffract light rays. Of course, interrupted circumferential rings may be used also.

The channels and microchambers can be constructed using an ultrafast laser. Such lasers use ultrafast pulses to process materials which may be in the nano or even femtosecond pulse range. Such pulse ranges instantaneously increase the melting, boring and vaporization temperature of the material. As such, a properly directed pulse can create the appropriate channels and microchambers. Commercially available suitable ultrafast lasers would be Spectra-Physics of Mountain View Calif.

What is claimed is:

1. A lens to be disposed on an eye, the lens having a back surface comprising:
   (a) an optic portion;
   (b) a scleral portion having an outer rim and an inner rim;
   (c) at least one generally arcuate groove in the back surface of the scleral portion that extends radially at least part of the distance between the outer rim and the inner rim, the at least one groove having a U-shaped cross section;
   (d) at least one circumferential groove disposed circumferentially in the back surface of the scleral portion; and
   (e) the at least one generally arcuate groove connects the at least one circumferentially disposed groove to at least one of the outer rim and the inner rim of the scleral portion.

2. The lens of claim 1 wherein the U-shaped generally arcuate groove extends the entire distance between the inner rim and the outer rim of the scleral portion.

3. The lens of claim 1 wherein the U-shaped groove is connected to at least one of the inner rim and outer rim by a microchannel that is smaller cross-section than the U-shaped groove.

4. The lens of claim 3 wherein the U-shaped groove is connected to both the inner rim and the outer rim by a microchannel.

5. The lens of claim 1, further comprising at least four U-shaped grooves disposed around the scleral portion of the lens.

6. The lens of claim 5 wherein the U-shaped grooves are spaced equally around the scleral portion of the lens.

7. A lens to be disposed on an eye, the lens comprising:
   an optic portion and a scleral portion, the scleral portion having an outer rim an inner rim, at least one generally arcuate groove formed in the back surface of the scleral portion, the at least one generally arcuate groove having a non-rectangular cross section; at least one circumferential groove disposed circumferentially on the back surface of the scleral portion and the at least one generally arcuate groove connects the at least one circumferentially disposed groove to at least one of the outer rim and the inner rim of the scleral portion.

8. The lens of claim 7 wherein the generally arcuate groove includes walls and a base, further comprising an angle greater than 90 degrees between at least one of the walls and the base.

9. The lens of claim 7 wherein the generally arcuate groove includes walls and a base, further comprising an angle less than 90 degrees between at least one of the walls and the base.

10. The lens of claim 7 wherein the generally arcuate groove is U-shaped and is connected to at least one of the inner rim and outer rim by a microchannel that is smaller cross-section than the U-shaped groove.

11. The lens of claim 10 wherein the U-shaped groove is connected to both the inner rim and the outer rim by a microchannel.

12. The lens of claim 10, further comprising at least four U-shaped grooves disposed around the scleral portion of the lens.

13. The lens of claim 12 wherein the U-Shaped grooves are spaced equally around the scleral portion of the lens.

* * * * *